US012685656B2

(12) United States Patent
Wu et al.

(10) Patent No.: US 12,685,656 B2
(45) Date of Patent: Jul. 21, 2026

(54) MEDICAL WALKING BOOT

(71) Applicant: Simple Medical (Shenzhen) Limited, Shenzhen (CN)

(72) Inventors: Hongshi Wu, Shenzhen (CN); Yong Liang, Shenzhen (CN)

(73) Assignee: Simple Medical (Shenzhen) Limited, Shenzhen (CN)

( * ) Notice: Subject to any disclaimer, the term of this patent is extended or adjusted under 35 U.S.C. 154(b) by 234 days.

(21) Appl. No.: 18/635,012

(22) Filed: Apr. 15, 2024

(65) Prior Publication Data

US 2025/0205070 A1      Jun. 26, 2025

(30) Foreign Application Priority Data

Dec. 25, 2023    (CN) .......................... 202323540832.6

(51) Int. Cl.
A61F 5/01          (2006.01)

(52) U.S. Cl.
CPC .......... A61F 5/0111 (2013.01); A61F 5/0195 (2013.01)

(58) Field of Classification Search
CPC ...... A61F 5/0111; A61F 5/0195; A61F 5/012; A61F 5/05816; A61F 5/34; A61F 5/0104; A61F 5/0102; A61F 5/01; A61F 5/00; A61F 5/0113; A61F 5/0127; A61F 5/04; A61F 5/058; A61F 5/05; A61F 5/0585; A61F 5/019; A61F 5/14
See application file for complete search history.

(56) References Cited

U.S. PATENT DOCUMENTS

| | | | | |
|---|---|---|---|---|
| 9,603,736 | B1 * | 3/2017 | Buck ...................... | A61F 5/0195 |
| 10,993,826 | B2 * | 5/2021 | Romo ................... | A61F 5/0102 |
| 2014/0259780 | A1 * | 9/2014 | Labonte ............... | A43B 5/0405 |
| | | | | 36/102 |

FOREIGN PATENT DOCUMENTS

| | | | | | |
|---|---|---|---|---|---|
| CN | 112274307 | A | * | 1/2021 | ........... A61F 5/0113 |
| EP | 1384568 | A1 | * | 1/2004 | ........... A43B 5/1683 |
| JP | 2021514702 | A | * | 6/2021 | ........... A61F 13/046 |

* cited by examiner

*Primary Examiner* — Tarla R Patel
(74) *Attorney, Agent, or Firm* — Birchwood IP

(57) ABSTRACT

A medical walking boot, having a boot body and a toes shield; the toes shield is removably connected with the boot body, so that a position of the toes shield relative to the boot body can be adjusted according to the needs of different users to suit different users.

5 Claims, 3 Drawing Sheets

MEDICAL WALKING BOOT

BACKGROUND OF THE INVENTION

The present invention relates to the field of medical products, and more specifically relates to a medical walking boot.

Medical walking boot is a fixation device for foot. Specifically, when a patient is suffered from bone fracture, joint dislocation, or foot sprain, a medical walking boot can be used to fix and protect the foot. Medical walking boot can also be used to rectify and cure a club foot. In order to adapt to toes of different sizes, an existing medical walking boot in the market, such as the one disclosed in CN219614151U (application No. 202320640546.8), will usually have an open front end which exposes user's toes. However, user's toes may then get hurt easily.

BRIEF SUMMARY OF THE INVENTION

In view of the aforesaid disadvantage now present in the prior art, the present invention provides a medical walking boot. The present invention is achieved through the following technical solutions:

A medical walking boot, comprising a boot body and a toes shield; the toes shield is removably connected with the boot body.

Further, the toes shield comprises at least one locking stud; the boot body comprises a plurality of locking holes arranged in at least one row where each row comprises more than one of said locking holes, and where each row is arranged linearly along a direction from a rear end of the boot body towards a front end of the boot body; said at least one locking stud is locked to at least one of said locking holes so that the toes shield is fixedly mounted to the boot body.

Further, left and right sides of the boot body are provided with inflating pumps respectively; an inflatable cushion is provided inside the boot body; the inflating pumps inflate the inflatable cushion.

Further, an air discharging valve is provided between each inflating pump and the inflatable cushion.

Further, strap buckles are provided on the boot body; a front strap is removably connected to and positioned between the strap buckles, and the strap buckles are fixed on the boot body; a rear strap is provided at a rear side of the boot body; a tightening device is provided between the boot body and each of two ends of the rear strap to loosen or tighten the rear strap.

Further, each tightening device comprises locking protrusions fixed to the boot body and a plurality of adjustment holes provided on a corresponding end of the two ends of the rear strap; by locking the locking protrusions to different adjustment holes, the rear strap can be loosen or tightened.

The present invention has the following beneficial effects: since the toes shield is removably connected with the boot body, a position of the toes shield relative to the boot body can be adjusted according to the needs of different users.

BRIEF DESCRIPTION OF THE DRAWINGS

In order to describe the technical solutions of the present invention more clearly, the drawings required to illustrate the embodiments of the present invention are briefly described below. Of course, the drawings as will be described below only illustrate some but not all of the possible embodiments. Given that no inventive effort is required, a person skilled in the art may obtain other drawings based on the drawings given in the present invention.

Figure 1:
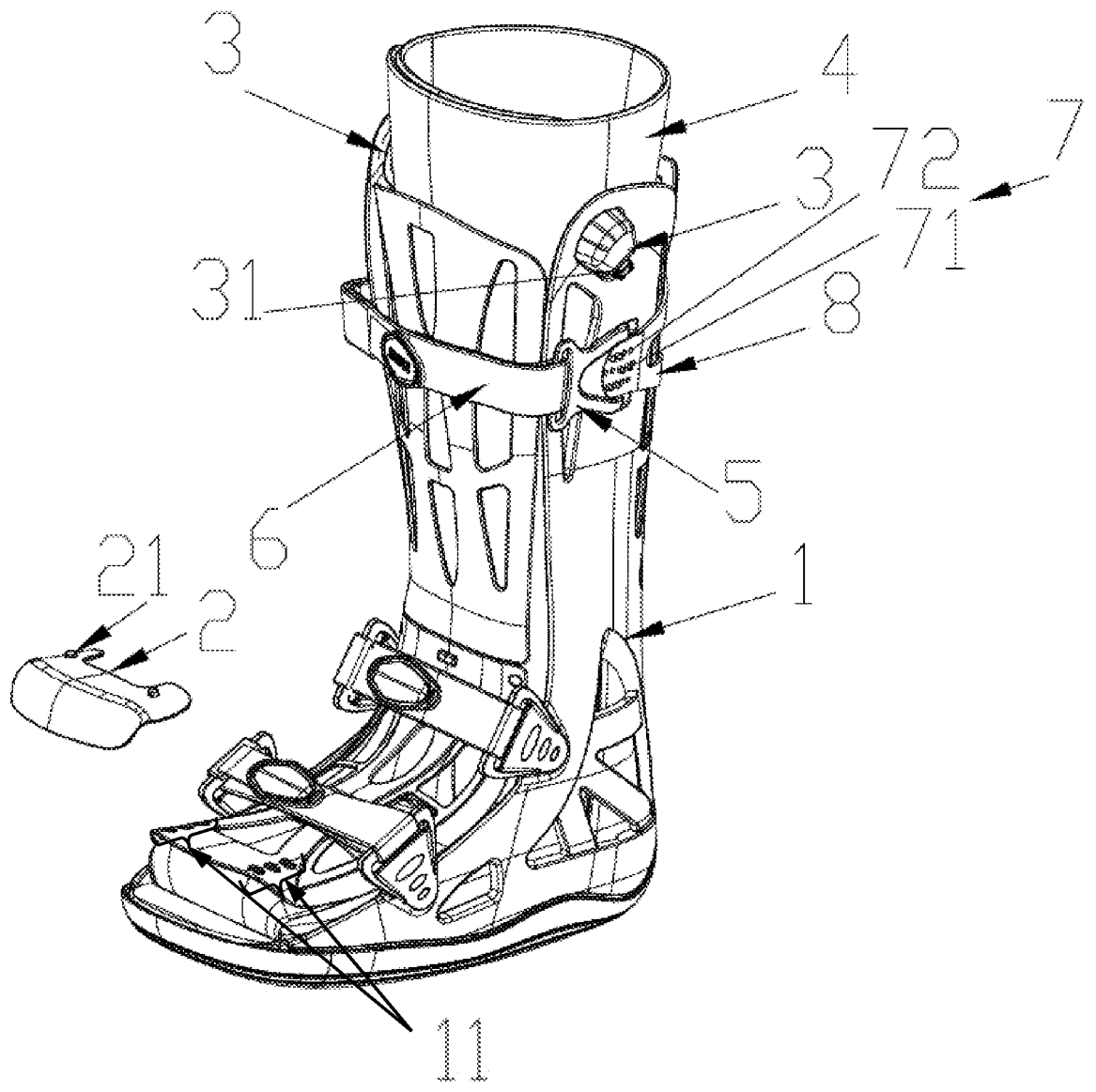
FIG. 1 is a partially exploded structural view of the present invention.

It should be noted that, the drawings may not be drawn in scale. The drawings are illustratively provided on condition that they will not affect the understanding of the invention by the readers.

DETAILED DESCRIPTION OF THE INVENTION

The embodiments according to the technical solutions of the present invention will be more clearly and thoroughly described below with reference to the drawings of the embodiments. Obviously, only some but not all of the embodiments of the present invention are described. Given that no inventive effort is required, any other embodiments obtained by a person skilled in the art shall also fall within the scope of protection of the present invention.

In the description of the present invention, it should be understood that orientations or positional relationships indicated by the terms "upper", "lower", "left", "right", "front", "rear", "top", "bottom", "inner", "outer", "middle", "vertical", "horizontal", "lateral", "longitudinal", and the like are orientations or positional relationships as shown in the drawings, and are only for the purpose of better describing the present invention and its embodiments instead of indicating and limiting that the devices, elements, or components in concern must have particular orientations, or be constructed and operated in the particular orientations.

Also, some of the terms mentioned above may contain other meanings apart from indicating orientations or positional relationships. For example, the term "upper" in some contexts may refer to a certain kind of interrelationship or connection. A person skilled in the art can understand the meaning of the terms in the description according to specific contexts.

Besides, the terms such as "mount", "provide", "comprise", "connect", "link", and the like should be interpreted in a broad sense. For example, it may be a fixed connection, a detachable connection or integration; may be a mechanical connection or an electric connection; or may be a direct connection, an indirect connection by means of an intermediate, or an internal interconnection between two devices, elements or components. For those of ordinary skill in the art, the specific meanings of the above terms in the present invention can be understood according to specific contexts.

In addition, the terms "first" and "second" are only for the purpose of distinguishing different devices, elements or components which may or may not be of the same type, and may or may not have the same structure. These terms should not be taken as indicating or implying the relative importance or the quantities of the described devices, elements or components. Unless otherwise specified, "plurality" means a quantity of two or above.

It should also be understood that, terms appearing in the description of the present invention are intended only for the purpose of describing specific embodiments, and shall not be taken as limiting the present invention. As used in the description and the claims, unless otherwise specified according to the contexts, features defined by "one", "a" and "the/said" also imply a quantity of more than one.

It should also be understood that, the term "and/or" used in the description and the claims is intended to mean any one of the described features, any combinations of the described features, all possible combinations of the described features, and a collection of these combinations.

Figure 2:
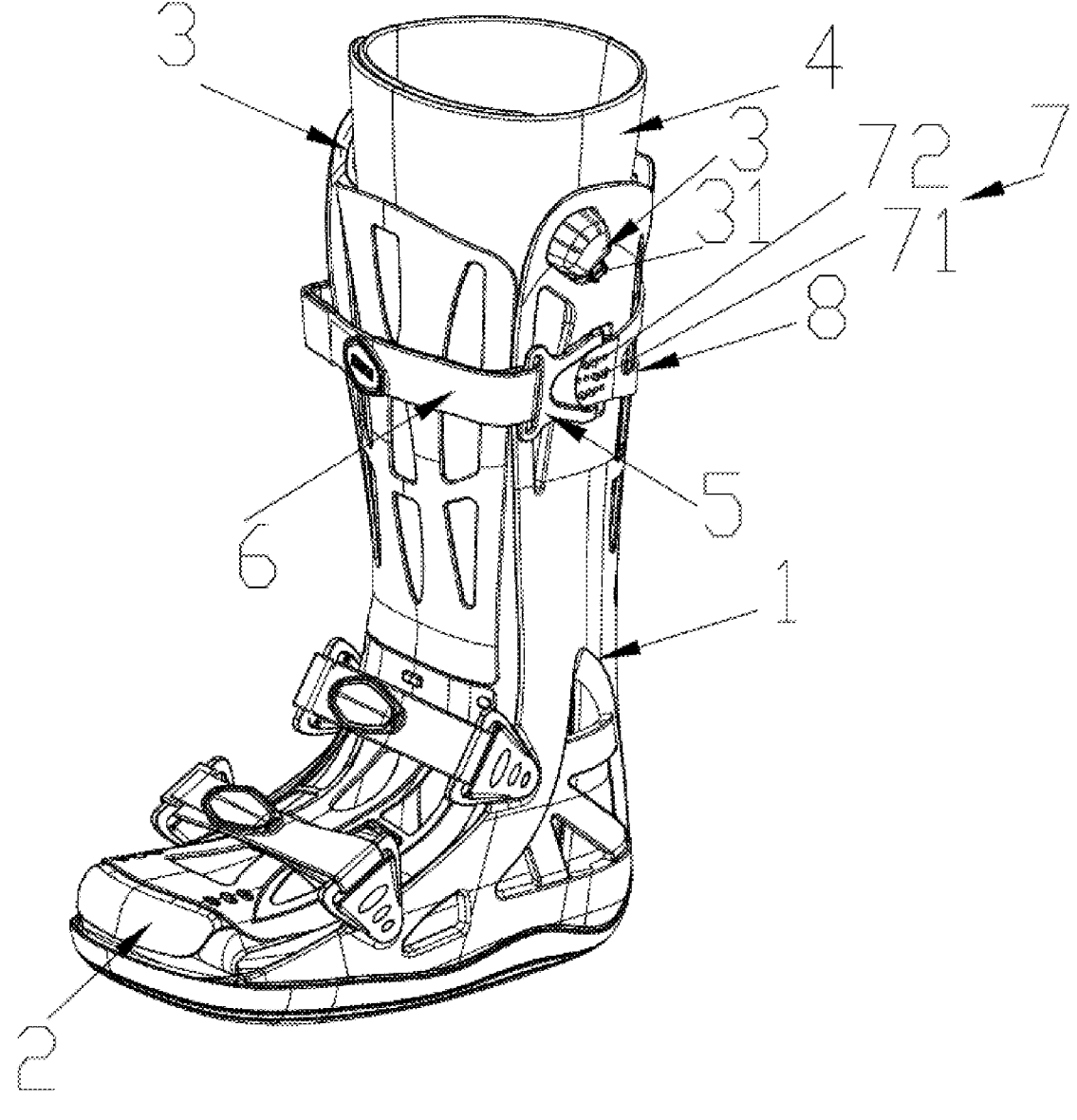
FIG. 2 is a schematic structural view of the present invention.
Figure 3:
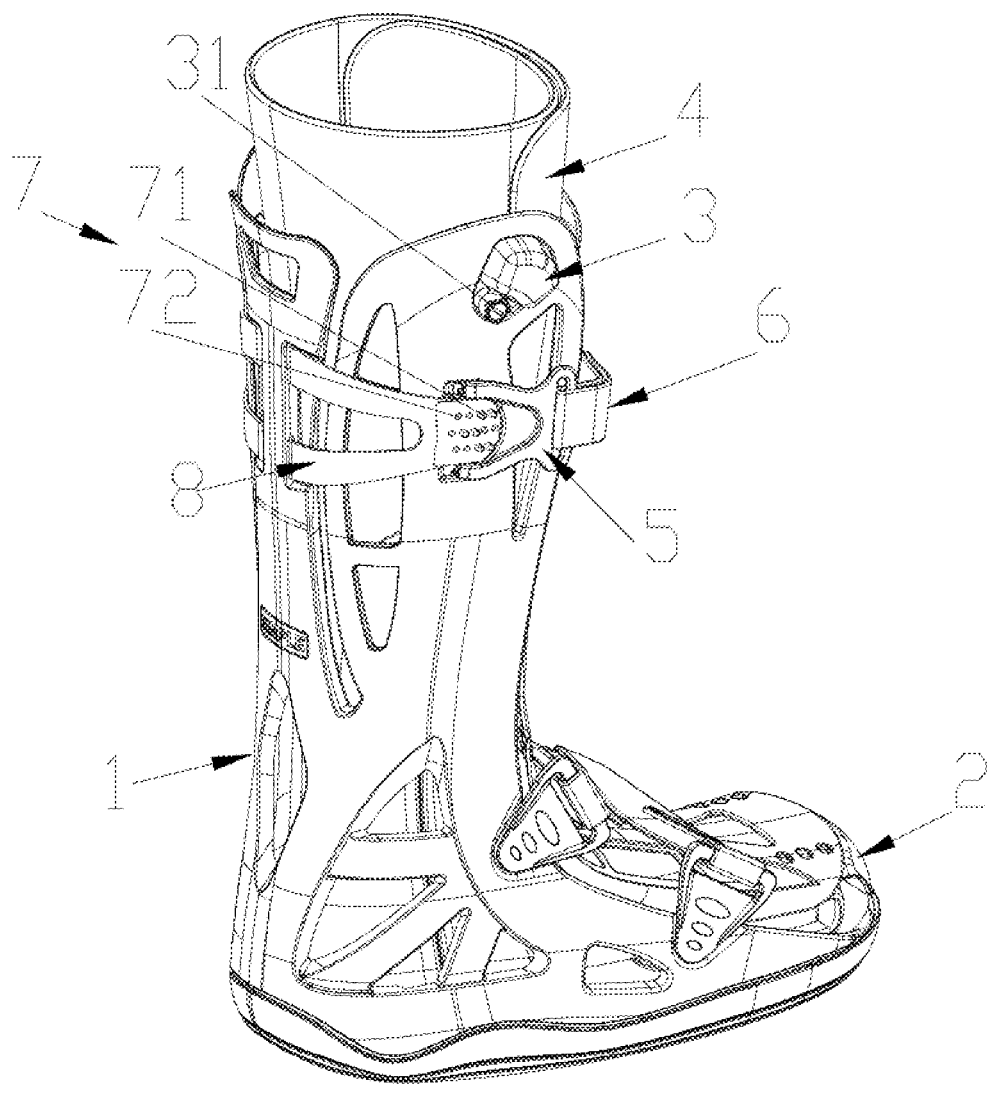
FIG. 3 is another schematic structural view of the present invention.

As shown in FIGS. 1-3, a medical walking boot comprises a boot body 1 and a toes shield 2; the toes shield 2 is removably connected with the boot body 1.

In the present invention, since the toes shield 2 is removably connected with the boot body 1, a position of the toes shield 2 relative to the boot body 1 can be adjusted according to the needs of different users.

Further, the toes shield 2 comprises at least one locking stud 21; the boot body 1 comprises a plurality of locking holes 11 arranged in at least one row where each row comprises more than one of said locking holes 11, and where each row is arranged linearly along a direction from a rear end of the boot body 1 towards a front end of the boot body 1; said at least one locking stud 21 is locked to at least one of said locking holes 11 so that the toes shield 2 is fixedly mounted to the boot body 1.

Further, left and right sides of the boot body 1 are provided with inflating pumps 3 respectively; an inflatable cushion 4 is provided inside the boot body 1; the inflating pumps 3 inflate the inflatable cushion 4.

Further, an air discharging valve 31 is provided between each inflating pump 3 and the inflatable cushion 4.

Further, strap buckles 5 are provided on the boot body 1; the strap buckles 5 allow a front strap 6 to be removably connected to the strap buckles 5, and the strap buckles 5 are fixed on the boot body 1; a rear strap 8 is provided at a rear side of the boot body 1; a tightening device 7 is provided between the boot body 1 and each of two ends of the rear strap 8 to loosen or tighten the rear strap 8.

Further, each tightening device 7 comprises locking protrusions 71 fixed to the boot body 1 and a plurality of adjustment holes 72 provided on a corresponding end of the two ends of the rear strap 8; by locking the locking protrusions 71 to different adjustment holes 72, the rear strap 8 can be loosen or tightened.

It should be understood that, in the embodiments of the present invention as described above, different embodiments and the features described therein can be combined to obtain new embodiments as long as no contradiction is resulted.

The more preferred embodiments of the present invention are described above. However, the above description is not intended to limit the present invention. The scope of protection of the present invention should be defined by the claims. The preferred embodiments of the present invention are not intended to limit the present invention. Minor changes or modifications resulting in other embodiments of equivalent technical effects may be possibly construed by a person skilled in the art in accordance with the teachings of the present invention without departing from the scope of the technical solutions of the present invention. Any non-inventive changes, changes or modifications that result in alternative embodiments achieving the same technical effects, made in accordance with the essence of the present invention without departing from the teachings of the present invention shall fall within the scope of the present invention.

What is claimed is:

1. A medical walking boot, comprising a boot body and a toes shield; the toes shield is removably connected with the boot body; the toes shield comprises at least one locking stud; the boot body comprises a plurality of locking holes arranged in at least one row where each row comprises more than one of said locking holes, and where each row is arranged linearly along a direction from a rear end of the boot body towards a front end of the boot body; said at least one locking stud is locked to at least one of said locking holes so that the toes shield is fixedly mounted to the boot body.

2. The medical walking boot of claim 1, wherein left and right sides of the boot body are provided with inflating pumps respectively; an inflatable cushion is provided inside the boot body; the inflating pumps inflate the inflatable cushion.

3. The medical walking boot of claim 2, wherein an air discharging valve is provided between each inflating pump and the inflatable cushion.

4. The medical walking boot of claim 1, wherein strap buckles are provided on the boot body; a front strap is removably connected to and positioned between the strap buckles, and the strap buckles are fixed on the boot body; a rear strap is provided at a rear side of the boot body; a tightening device is provided between the boot body and each of two ends of the rear strap to loosen or tighten the rear strap.

5. The medical walking boot of claim 4, wherein each tightening device comprises locking protrusions fixed to the boot body and a plurality of adjustment holes provided on a corresponding end of the two ends of the rear strap; by locking the locking protrusions to different adjustment holes, the rear strap is loosen or tightened.

* * * * *